US009568428B2

(12) United States Patent
Thomas et al.

(10) Patent No.: US 9,568,428 B2
(45) Date of Patent: Feb. 14, 2017

(54) DIAGNOSTIC INSTRUMENT AND FLOW PROCESS

(75) Inventors: Richard A. Thomas, Miami, FL (US); Michael W. Brochu, Jr., Coral Springs, FL (US); Michael L. Brochu, Sr., Fort Lauderdale, FL (US); Ernest R. Thomas, Miami, FL (US); Michael A. Thomas, Davie, FL (US)

(73) Assignee: Beckman Coulter Biomedical, LLC, Washington, DC (US)

( * ) Notice: Subject to any disclaimer, the term of this patent is extended or adjusted under 35 U.S.C. 154(b) by 440 days.

(21) Appl. No.: 13/696,274

(22) PCT Filed: May 5, 2011

(86) PCT No.: PCT/US2011/035417
§ 371 (c)(1),
(2), (4) Date: Jan. 22, 2013

(87) PCT Pub. No.: WO2011/140387
PCT Pub. Date: Nov. 10, 2011

(65) Prior Publication Data
US 2013/0143309 A1     Jun. 6, 2013

Related U.S. Application Data (60) Provisional application No. 61/331,787, filed on May 5, 2010, provisional application No. 61/331,782, filed on May 5, 2010.

(51) Int. Cl.
*G01N 33/00* (2006.01)
*G01N 21/64* (2006.01)
*G01N 15/14* (2006.01)
*G01N 35/00* (2006.01)

(52) U.S. Cl.
CPC .......... *G01N 21/6486* (2013.01); *G01N 15/14* (2013.01); *G01N 35/0092* (2013.01); *G01N 35/00623* (2013.01)

(58) Field of Classification Search
CPC .......... B01F 9/06; B01F 15/0291; B01F 3/502
(Continued)

(56) References Cited

U.S. PATENT DOCUMENTS 5,589,649 A * 12/1996 Brinker et al. ................. 73/866
6,296,764 B1 * 10/2001 Guirguis et al. ........... 210/323.1
(Continued)

FOREIGN PATENT DOCUMENTS

CN       101073002 A     11/2007
JP       2005-180831 A    7/2005
(Continued)

OTHER PUBLICATIONS

European Search Report for Application No. 11778379.5 mailed Aug. 6, 2013.
(Continued)

*Primary Examiner* — Jill Warden
*Assistant Examiner* — Brittany Fisher
(74) *Attorney, Agent, or Firm* — Merchant & Gould P.C.

(57) ABSTRACT

A diagnostic instrument having a cellular analysis system capable of running standardized immune monitoring panels. The system could include an automated and integrated specimen sampling method through a continuous flow process. The instrument could include a probe washer station, scheduler, cassette autoloader, bar coding system, and/or containment area common interface. An improved optimization test is proposed for instrument and flow cytometer quality assurance. The proposed method analyzes population separation for measuring instrument performance and/or sample quality. Such a method may also use population separation for measuring sample and/or run quality.

9 Claims, 6 Drawing Sheets

(58) Field of Classification Search
USPC .......................................... 422/513; 73/1.74
See application file for complete search history.

(56) References Cited

U.S. PATENT DOCUMENTS

| | | | |
|---|---|---|---|
| 6,830,935 B1 * | 12/2004 | El-Amin et al. .............. | 436/177 |
| 2006/0250604 A1 * | 11/2006 | Hamada et al. ................ | 356/39 |
| 2007/0048185 A1 | 3/2007 | Dupoteau et al. | |
| 2008/0031776 A1 | 2/2008 | Sevigny et al. | |
| 2009/0122311 A1 * | 5/2009 | Kanda ........................... | 356/318 |
| 2010/0035349 A1 | 2/2010 | Bau et al. | |
| 2010/0066996 A1 | 3/2010 | Kosaka et al. | |
| 2010/0068723 A1 | 3/2010 | Jovanovich | |
| 2012/0195812 A1 | 8/2012 | Nagai et al. | |

FOREIGN PATENT DOCUMENTS

| | | |
|---|---|---|
| JP | 2007-503580 A | 2/2007 |
| JP | 2007-139462 A | 6/2007 |
| JP | 2007-527011 A | 9/2007 |
| JP | 2009-216410 A | 9/2009 |
| JP | 2010-038659 A | 2/2010 |
| JP | 2010-066996 A | 3/2010 |
| RU | 2217498 C2 | 11/2013 |
| WO | 2005-093432 A2 | 10/2005 |
| WO | 2009114514 A2 | 9/2009 |
| WO | WO 2009/114514 | 9/2009 |
| WO | WO 2011/140390 A2 | 11/2011 |

OTHER PUBLICATIONS

"Fully Automated Load & Go CR Series Immune Monitoring Systems," Blue Ocean Biomedical, LLC, Pembroke, Pines, Florida, 6 pages (2010).

Wulff, S., Editor, "Guide to Flow Cytometry," Dako, Carpinteria, California, 130 pages (Copyright 2006).

International Search Report for International Application No. PCT/US11/35417 mailed Sep. 29, 2011.

* cited by examiner

DIAGNOSTIC INSTRUMENT AND FLOW PROCESS

This application is a National Stage Application of PCT/US2011/035417, filed May 5, 2011, which claims benefit of U.S. Provisional Ser. No. 61/331,787 and U.S. Provisional Ser. No. 61/331,782 filed 5 May 2010 and which applications are incorporated herein by reference. To the extent appropriate, a claim of priority is made to each of the above disclosed applications.

BACKGROUND OF INVENTION

The present invention relates generally to a diagnostic instrument and quality assurance system for a diagnostic instrument, and more specifically to a cellular analysis diagnostic instrument having a spectrum analyzer such as a flow cytometer, and a quality assurance system therefor.

SUMMARY OF INVENTION

Cellular analysis instruments using flow cytometers are known in the field. See, for example, U.S. patent application Ser. No. 11/825,523, incorporated herein by reference. A flow cytometer directs a flow of particles through a sensing zone where the particles can be excited by a beam of light. The beam of light causes the particles to fluoresce and/or scatter light, and the emitted light is separated by filters into portions of the electromagnetic (EM) spectrum. By studying the filtered EM spectrum, analyses of the cellular content can be performed and certain characteristics and values can be reported.

In one illustrated embodiment, the proposed system relates to a fluorescence-based, cellular analysis system capable of running standardized immune monitoring panels. The proposed system combines automated specimen/sample preparation (e.g. blood samples, bone marrow, tissue, serum, urine, synovial, spinal, peritoneal, plural, or any other type of fluid or sample) and analysis in a single, compact instrument. The single instrument provides improved accuracy, minimal clinician interaction (and therefore minimal clinician training), faster processing time, and processing options ranging from single-sample to a plurality of samples processing. Advantageously, such a plurality of samples may be processed and analyzed continuously.

A specimen autoloader can be provided for moderate-to-high volume laboratories. According to the embodiments disclosed herein, clinicians can load sample tube(s) into the system (either via autoloader or single-sample insertion through a front door) and walk away, with no need for follow-up. For example, a clinician would not need to return to transfer samples between preparation and analysis instruments and computers, because the single instrument would be able to perform all of those steps, in precisely the order and timing required by the tests to be performed. Additionally, the proposed system would allow for a number of types of tests to be performed on each sample, without slowing down or impacting the tests that are performed on adjoining or subsequent samples. For example, hypothetical Sample A could receive tests 4, 5, and 6, that require durations of 5, 7, and 15 minutes respectively, while hypothetical Sample B could receive tests 4, 7, and 8, requiring durations of 5, 10, and 8 minutes respectively.

Using the proposed device, both hypothetical samples A and B (as well as other samples) could be loaded at the same time, and the sample preparation could begin in the order received. Preparation would be followed by sample analysis, such that Sample A might begin analysis as Sample B is finishing its preparation. All actions related to the different sample preparations and analysis could be performed without clinician intervention. Furthermore, the analysis of data for obtaining reportable results is automated (i.e. setting of gates, regions, and cursors as well as flagging or notification of suspect results).

Moreover, a clinician could insert additional samples at any time, and such samples could be advanced above any samples waiting in the autoloader should the clinician so desire. In summary, a user can put a sample into the proposed device at any time, and the reaction timings, analysis timing, and all other sequences will be handled by the proposed device. Because each sample may have a completely different set of parameters, reaction times, reagents, and analyses to be performed, the proposed device would track all of this data and process each sample according to the specific requirements applicable to the sample and the desired test(s).

In another illustrated embodiment, a quality assurance system can be applied to a fluorescence-based, cellular analysis system capable of running standardized immune monitoring panels. The proposed system can be used in combination with automated specimen/sample preparation (e.g. blood samples, bone marrow, serum, urine, synovial, spinal, peritoneal, plural, or any other type of fluid or sample) and analysis that might be completed, for example, in a single, compact instrument.

Early flow cytometers were custom built machines, and were often considered marginally stable. Eventually, flow cytometers were manufactured by companies selling equipment such that one could acquire two instruments that were built the same. However, flow cytometers were still very sensitive instruments, and keeping the instrument in full alignment (i.e. optically optimized) was still a challenge. Eventually, the challenges associated with keeping the instrument optically optimized were minimized with newer technologies; however, the issue still exists in the flow cytometry industry, and most flow cytometry labs will perform a test at the beginning of each day of procedures to confirm optimization.

Procedures for running tests on flow cytometers have traditionally focused on ensuring that the flow cytometer was optically optimized. Manufacturers and clinics have long relied upon fluorescent "beads" (aka "microspheres") to measure the optimization of a flow cytometer. In summary, the test would show whether a flow cytometer could detect the difference between types of fluorescent beads. It was proposed that such beads had relevance to the actual operation of flow cytometer, even though the data reported was not necessarily that which would be typical for the clinical tests to be performed.

The bead test would then be followed by another test to ensure that the reagents used were performing properly. Users with training in the art of flow cytometers were required to make the determinations—largely based on experience or their own insight—as to whether the flow cytometer was sufficiently "optimized" such that it could perform the required diagnostic tests that day.

An improved optimization test is proposed for instrument and flow cytometer quality assurance. The proposed method analyzes population separation for measuring instrument performance (using software calculations of off light scatter, ECV and/or fluorescence). Another method may be employed for sample quality assurance. Such a method may also use population separation for measuring sample and/or run quality using similar software calculations of off scatter, ECV and/or fluorescence.

Additional features of the disclosure will become apparent to those skilled in the art upon consideration of the following detailed description of preferred embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
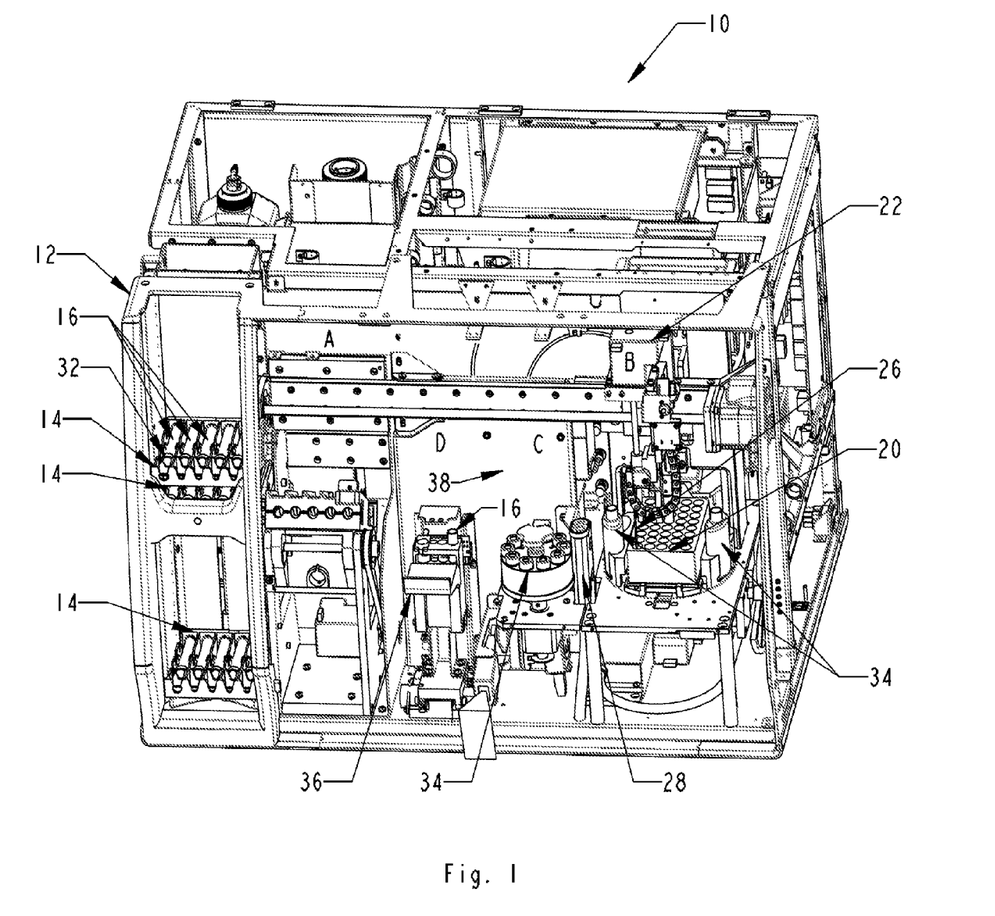
FIG. 1 is a perspective view of one embodiment of a diagnostic instrument, wherein the instrument is shown coupled with a specimen autoloader and includes a flow cytometer.
Figure 2:
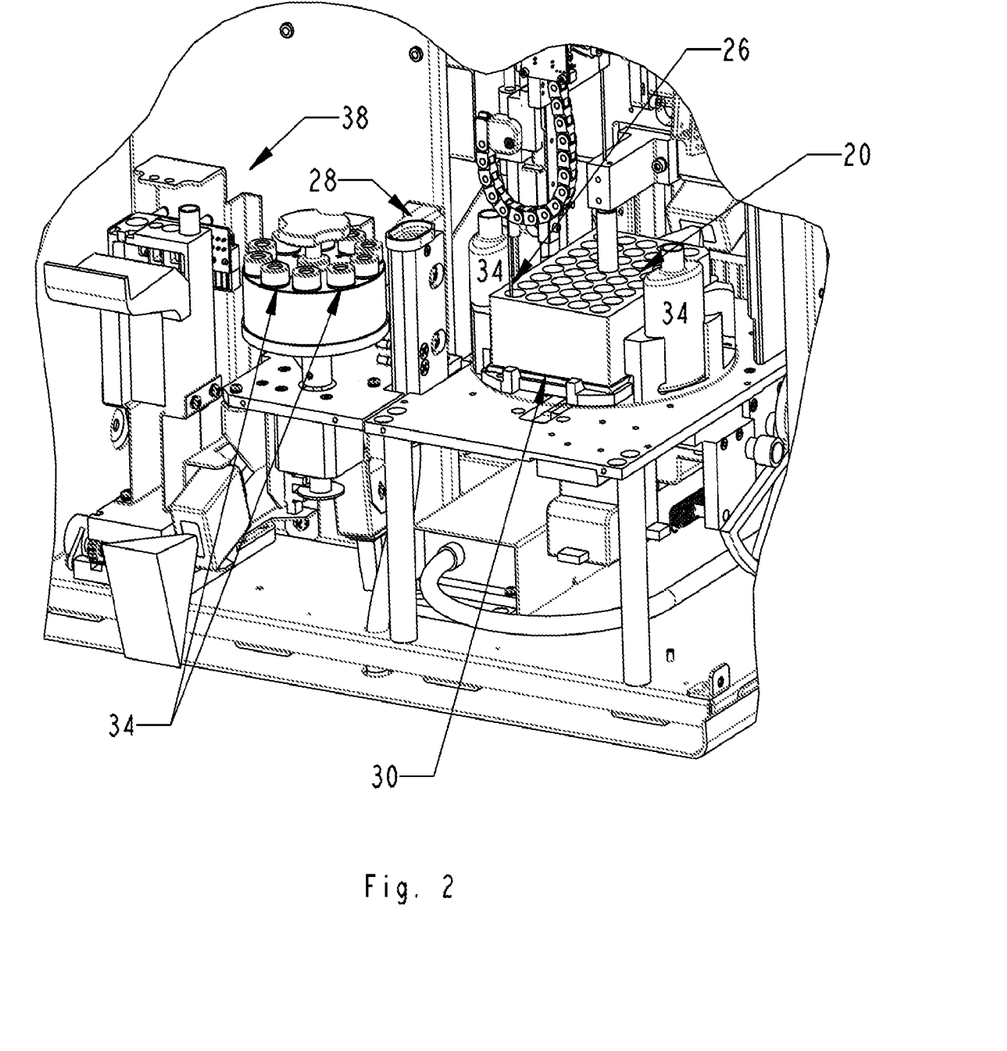
FIG. 2 is an enlarged perspective view of a portion of the diagnostic instrument shown in FIG. 1.
Figure 3:
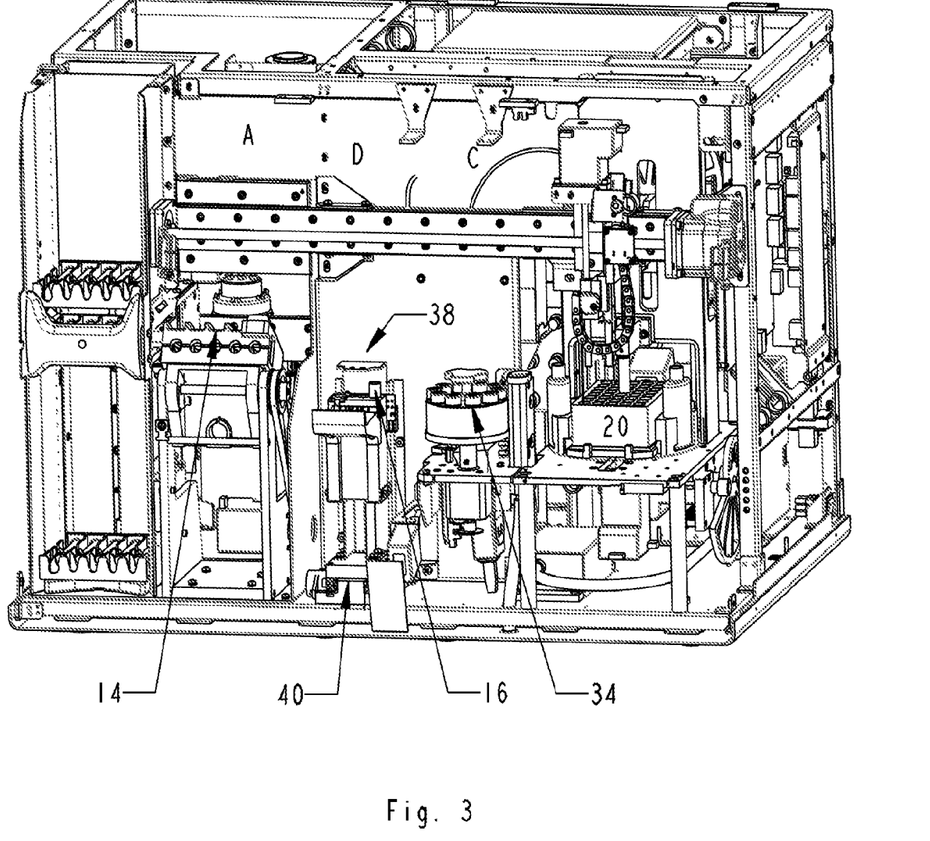
FIG. 3 is a front perspective view of the diagnostic instrument of FIGS. 1-2, showing the instrument during operation.
Figure 4:
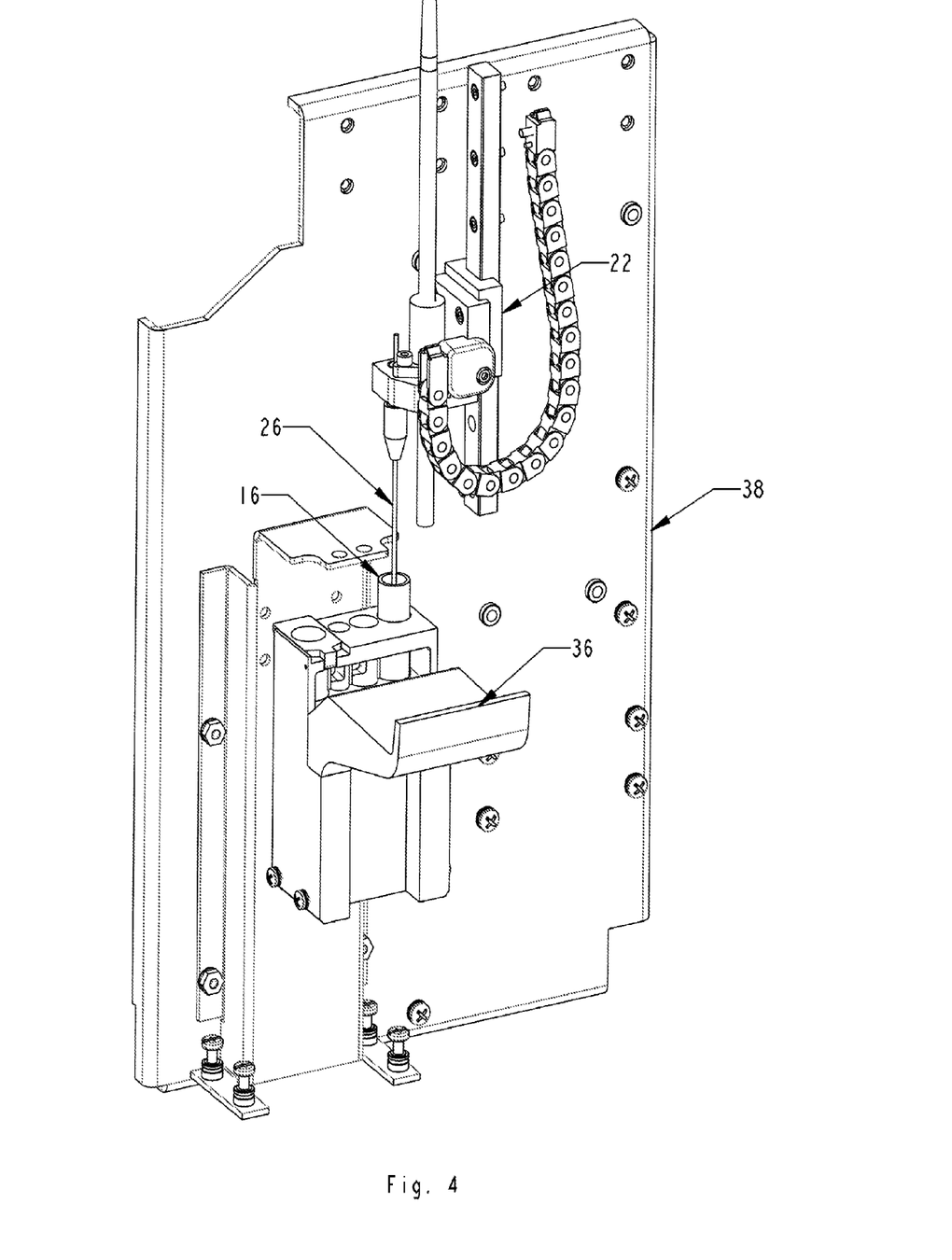
FIG. 4 is an enlarged view of the portion of the diagnostic instrument that is capable of sampling a single specimen tube at a time.
Figure 5:
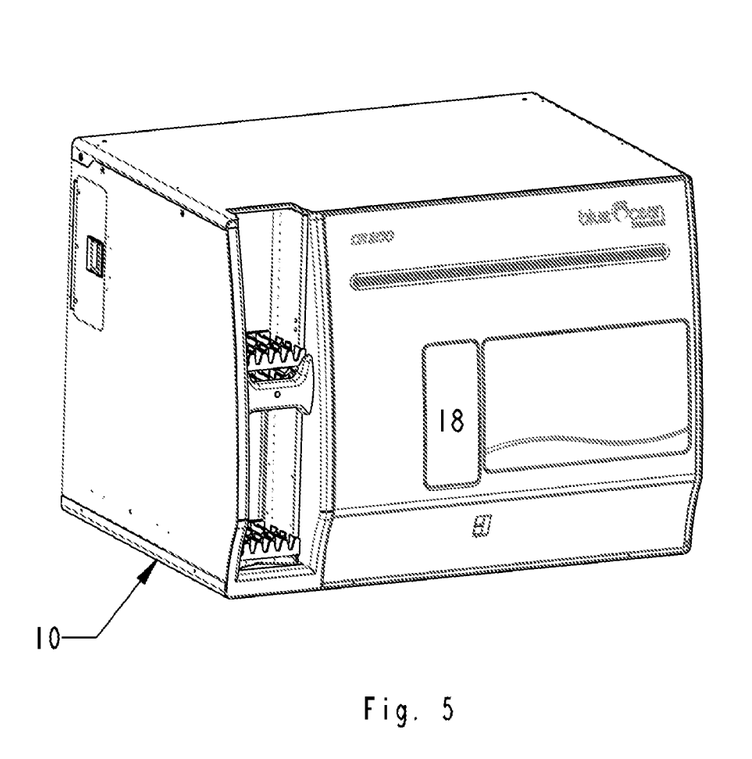
FIG. 5 is a front perspective view of the external housing of the proposed diagnostic instrument shown in FIGS. 1-4.
Figure 6:
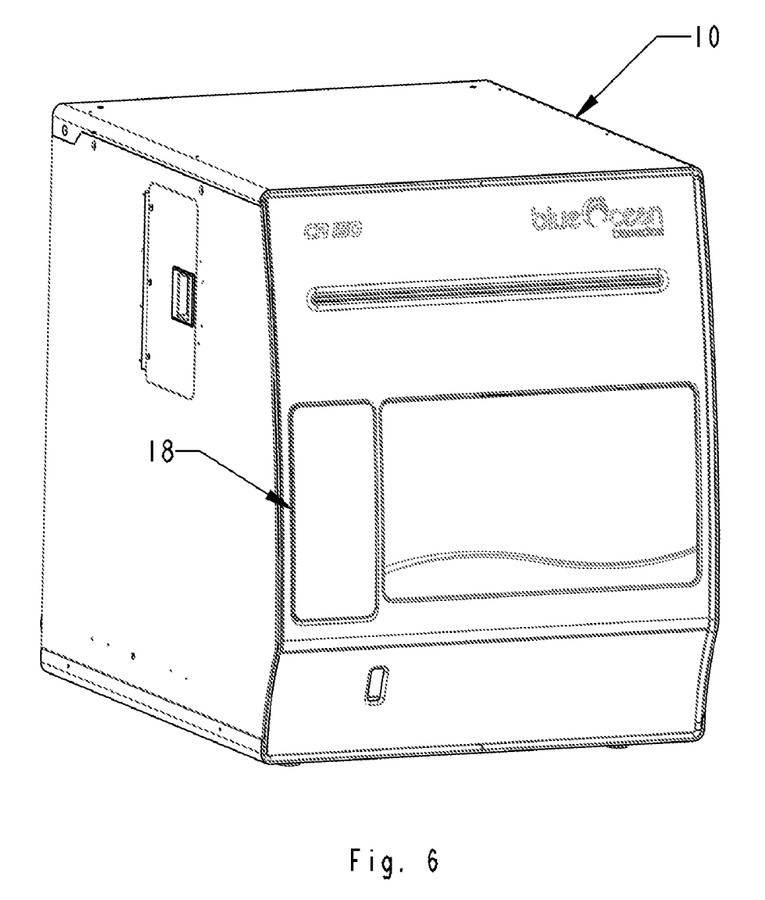
FIG. 6 is a front perspective view of the external housing of another embodiment, in which the specimen autoloader is removed and specimen tubes are inserted through the front door.

One embodiment of the present disclosure is shown in FIGS. 1-6 in the form of a diagnostic instrument 10. In the illustrated embodiment, an autoloader portion 12 can be seen having a number of specimen cassettes 14 loaded thereon. In such an embodiment, cassettes 14 can be loaded with a plurality of identical specimen tubes or vials (hereinafter referred to as "tubes") 16, a variety of specimen tubes 16, or merely a single specimen tube 16. The cassettes are then top-loaded into autoloader portion 12 and processed in the order received. In the alternative, i.e. when faster, single-sample processing is desired, a specimen tube can be inserted directly into an alternative specimen entry point, i.e. door 18 (visible in FIG. 5) and processed ahead of any awaiting cassettes 14, as shown in FIG. 4. This provides for stat access to the testing by a clinician, with a capability to run tests immediately, thereby interrupting (but not negatively affecting) testing of other specimen tubes when desired by the clinician. Additionally, a specimen tube that has compromised or no bar coding (discussed infra) may be inserted manually.

As described in detail below, diagnostic instrument 10 illustratively performs the following steps once a specimen tube 16 (or specimen tube cassette 14) is received. It is contemplated that such steps are performed by instrument 10 without intervention by a clinician, and the steps may be modified, added to, or eliminated depending on the particular test(s) to be performed. It should be understood that while blood tubes are discussed throughout the disclosed embodiment, it is contemplated that other types of body fluids and samples are within the scope of the disclosure, and capable of being analyzed in the proposed instrument 10. For example, bone marrow, serum, urine, synovial, spinal, peritoneal, plural, and other types of fluids or samples may be tested and analyzed substantially as described below.

Mixing (e.g. rocking) samples while still in specimen tubes 16 (in the autoloader embodiment)

Piercing the cap of specimen tubes 16 and sampling the requisite amount of the specimen Reading barcodes (or any other form of marking/identifying) to confirm sample/patient ID and/or to confirm type/size of tube Matching ID, test(s) to be performed, & reagents required, and assigning a serial number for tracking by the computer Placing the specimen/sample in selected empty tubes or wells in a containment area 20 (shown, for example, as a microtiter plate in FIGS. 1-3), for further processing Adding appropriate reagents in the appropriate sequence and timing so as to properly prepare the samples for the tests to be performed Allowing the samples to react with reagents for prescribed incubation times (variable based on the reagent)

Splitting the sample into a plurality of tubes/wells in the containment area 20 (if desired or required by testing)

Tracking all samples, cassettes, reagents & relevant positions via barcodes or other type of tracking device (e.g. RFID)

Timely aspirating the prepared sample/reagent combination from the containment area and analyzing it via flow cytometer (while preparing subsequent samples)

Auto-verifying results or holding results for review, depending on clinician-initiated decision rules.

Instrument 10 is designed to provide automated and integrated specimen sampling, meaning that each of the above steps (if required by the particular tests) can be carried out within and by instrument 10, without the use of additional diagnostic equipment. Moreover, if desired by the clinician, such steps can be done without any interaction from the clinician. It should be understood, however, that instrument 10 may be configured to alert a clinician in the event of a fault or other problem.

In the illustrated embodiment, instrument 10 uses a single-axis probe carrier 22 that permits various functions to be performed while probe carrier 22 is moved along single-axis track 24. For example, probe carrier 22 (and therefore probe 26) can be positioned to draw samples from tubes 16 when probe carrier 22 is in position A, can deposit the samples in containment area 20 at position B, and can sample reagents at position C. If a sample is placed in pivotable tray 36 at any point (i.e. for stat processing of a sample), instrument 10 will sense the presence of the sample and insert it ahead of any samples awaiting processing in the autoloader 12. Probe carrier 22 will then move to position D so that probe 26 can sample from the tubes placed in pivotable tray 36. Reagents are deposited in containment area 20 either before or after the sample is deposited (or both before and after) for reaction with the sample as required by the particular test(s) to be performed and may be themselves tracked as discussed below.

The steps may be performed in the following order. However, it is contemplated that certain tests may skip one or more steps, or may modify a step in order to achieve the best test results for the desired blood test(s).

First, specimen tubes 16 may be loaded into a pre-configured cassette 14 that is appropriate for the particular specimen tubes 16 to be used. For example, specimen tubes 16 may be a commonly found size of 13 mm×75 mm specimen tube, in which case the five-tube cassette 14 shown in FIGS. 1 and 3 may be used. However, it should be understood that a variety of sizes and types of specimen tubes 16 may be used with the present invention, and cassettes 14 may be designed accordingly. A cassette 14 may even be configured to hold a variety of specimen tubes 16. As stated above, various sizes of specimen tubes 16 may also be inserted individually through door 18, shown in FIG. 5.

If specimen tubes 16 have a cap 32, the specimen tubes (held by cassette 14) may be rocked such that the blood is stirred inside the tube and made more homogenous (for more accurate sampling). Such rocking occurs at station A, and cassette 14 can be seen in its rocked position in FIG. 3.

During rocking of cassette 14, probe carrier 22 may be directed to move to station C and begin sampling the appropriate portions of reagents 34 for the tests to be performed. However, if the test does not contemplate reagents 34 being placed on the containment area 20 prior to the blood sample, then probe carrier 22 may perform such step after sampling the blood from tube 16.

Reagents 34 may be held in vials, as can be seen at position C. However, reagents may alternatively or additionally be held in reservoirs positioned elsewhere, such as on the plate base 30 (shown in FIGS. 1-2), or in other areas (not visible) that can be, for example, plumbed directly to probe 26.

As set forth above, diagnostic instrument 10 also contemplates that a clinician can insert a specimen tube 16 via external door 18. To accommodate this, a tube receiver 38 is provided in illustrated instrument 10, and such tube receiver may accommodate a variety of types of specimen tubes 16, including pediatric tubes, as can be seen in FIGS. 2-4. In the illustrated example, specimen tubes 16 are held by a pivotable tray 36 that permits easy access and retrieval of specimen tubes 16. In an alternative embodiment, shown in FIG. 3, specimen tubes 16 may be held by a rotatable cassette 40.

In between and after sampling of specimens and/or reagents 34, probe carrier 22 may move to a probe washer station 28, so that probe 26 can be washed. Washing the probe 26 prevents cross-contamination and therefore prevents inaccurate test results.

After sufficient mixing is done of the specimen within the tubes (i.e. at station A), the specimen is sampled by probe 26 and deposited in predetermined wells or tubes in containment area 20. Depending on the test(s) to be performed, specimen samples may be placed in more than one well or tube, and the corresponding amount of specimen (such as blood) may be aspirated in advance. Probe 26 is then washed at washer station 28 as described above.

Depending on whether or not reagents are added to the specimen samples after depositing them in containment area 20, the probe carrier 22 may be moved to station C for sampling of the appropriate reagent(s) 34. Again, if more than one reagent is needed, probe 26 is washed at washer station 28 between each reagent 34 sampling and after the final reagent 34 sampling.

In order to deposit specimen samples and reagents in each well or tube of containment area 20, plate base 30 may be positioned on a rotating axis so that each well or tube could be presented to probe 26, depending on the point of rotation of the plate base 30. Such a configuration and rotational movement of plate base 30 is disclosed in U.S. patent application Ser. No. 11/804,721, incorporated herein by reference.

While it is contemplated that a multi-axis probe carrier may also accomplish these goals, certain advantages exist for a single-axis device. For example, a single axis device requires fewer parts and less programming, yields a smaller instrument 10 footprint, is easier to align, is more reliable and more stable, and ultimately faster in its movement between stations.

After placement in wells or tubes, the specimen samples are left to react with reagents for a specific amount of time (depending on the reagents and the tests to be performed) and then processed through the flow cytometer for analysis. It is contemplated that other test equipment may also be incorporated, such as equipment that uses electronic volume for cell sizing and differentiation, or hemoglobin measurement using absorbance.

Conveniently, containment area 20 serves as a common interface between sample preparation and analysis. Moreover, containment area 20 can include fixed or detachable, and/or disposable or reusable components, allowing a clinician to opt to throw away the entire interface (as in the example of a microtiter plate) after use. By serving as the common interface between the preparation arm and analysis arm, containment area 20 provides a system with less exposure to mistakes and external or environmental influences.

A processor and software scheduler configured to run on the processor (not shown) are also incorporated in the disclosed system. The software scheduler may be programmed, for example, to recalculate available windows for fixed reaction kinetics (optimizing throughput while maintaining reproducible reaction kinetics) (i.e. antibody incubations, RBC lysing time, reaction quench time, etc.).

It is also contemplated that numerous items can be barcoded and tracked during operation. Such barcoding and tracking can be registered by the software scheduler. For example, barcodes may be assigned to the reagent vials 34, specimen tubes 16 (with different bar codes for different patients and/or sizes), sheath fluids, common interfaces (i.e. containment areas 20), preparation reagents, bead reagents, cassettes 14, etc. By bar coding these various items, a variety of significant information can be tracked, such as reagent usage/consumption, how many tests remain for each reagent bottle, open container expiration, closed container expiration, assay values, etc.

The software scheduler may be configured to perform the following steps.

Decide if it is ok to add a new sample at this time or not, and hold off door or multi-loader (random access) if another activity needs to take precedence.

Minimize the sample door 18 unavailable effect by adjusting non-kinetic reactions if any, or kinetic reactions that have a broader acceptable window.

Minimize collision effects, and optimize throughput by defining acceptable windows for each kinetic reaction.

Force analysis to take a predetermined amount of time (stop on time/fixed volume of sample)

Use predetermined times for each cycle, (acquiring of blood, adding of reagents including mixing, analysis) so all activities can be properly scheduled.

Take all scheduled sample time windows into effect in determining if it is acceptable to add a new sample to the schedule, and schedule such new sample so that all its activities take place at the predetermined times.

Take hardware resources and physical hardware collisions into effect in determining if the schedule can be accomplished.

Using instrument 10 in combination with the software scheduler disclosed herein, a Time to First Result (TFR) can be less than 15 minutes, with subsequent results reported about every 90 seconds. Throughput can be more than 300 samples per day, and results can be reported much quicker and earlier in the day, so a lab's capacity can be significantly increased.

In the illustrated embodiment, the analysis of data for obtaining reportable results is automated (i.e. setting of gates, regions, and cursors as well as flagging or notification of suspect results). The flagging/notification aspect may be referred to as an auto-verify feature in the system.

With all sample preparation and analysis fully integrated in one instrument 10, a clinic need not perform slow and tedious "batch processing," where the samples are collected and processing started once a sufficient number are collected—progressing through each step of the blood processing with the entire group of samples. In contrast, instrument 10 is configured to automatically prepare patient samples in containment area 20, so there are no daughter tubes to label and keep track of, and significantly less blood and reagents are needed. Samples can be loaded onto the system at any time, and in the illustrative embodiment, each will be automatically processed and exit the system pipeline in approximately 15 minutes. Subsequent samples could exit the system pipeline in approximately 90 second intervals, although exact times will vary depending on the tests to be performed and required sample preparation times.

A significant advantage is the cost savings for a lab. Not only can more samples be processed in a single day, by using one system, there are lower system costs, lower reagent costs and reduced hands-on labor. Accordingly, the overall cost to own and operate the instrument 10 is significantly lower.

Prior art processes and systems, with their multiple modules and computer screens, take up between 10 and 13 feet of valuable bench space. In contrast, diagnostic instrument 10 is compact, measuring only 31 inches wide, inclusive of the autoloader portion 12. The embodiment shown in FIG. 6, without an autoloader portion, requires an even smaller footprint. A touch-screen computer/screen (not shown) can also be conveniently placed on top of the system, keeping the footprint small and freeing up valuable space for the lab.

It is contemplated that the proposed system may be ideal for clinical researchers running one or more fixed immune surveillance panels for contract research, pharmaceutical drug development, and research in university medical centers and reference labs. It is further contemplated that the standardized immune monitoring panels may be monitoring for immunodeficiency (HIV-AIDS), autoimmune diseases, organ transplant response, infectious diseases, oncology and others.

A frequent concern with diagnostic devices having flow cytometers is that the optics in the flow cytometer tend to become less optimized over time. Accordingly, what is needed is a method of testing various aspects of performance that can be correlated to the actual tests that are to be performed by the flow cytometer device.

In general, two characteristics contribute to performance:
1. Resolution (the ability to measure two particles with the same quantity of fluorescence and assign them the same value); and
2. Sensitivity (ability to differentiate between a dim particle and a slightly brighter particle)

In order to measure these characteristics, "microspheres" or "beads" are commonly used in the industry. These microspheres are typically constructed from, for example, fluorophore-labeled materials that have known fluorescence values. When such microspheres are passed through a flow cytometer, certain tests have been performed that reflect the resolution and sensitivity values being measured by the flow cytometer.

The bead test is then typically followed by another test to ensure that the reagents used are performing properly. Users with training in the art of flow cytometers make determinations—largely based on experiences or their own (variable) insights—as to whether the flow cytometer was sufficiently "optimized" such that it could perform the required diagnostic tests that day.

Often, the diagnostic tests to be performed by a flow cytometer will have different minimum resolution and sensitivity needs than the bead and reagent tests that are dominant in the industry. It is often the case that the bead and reagent tests will indicate to a clinician that the flow cytometer is not optimized, whereas in reality, the flow cytometer is operating sufficiently to perform the diagnostic tests required—it simply didn't pass the hypothetical bead and reagent tests.

Therefore, it is desirable to utilize a known patient sample, for example a blood control, so that any deficiency in resolution or sensitivity can be narrowed down to the reagents and instrument performance. When a known patient sample is used, for example a blood control, only the reagents and instrument performance can affect the resolution and sensitivity outcomes of the test.

According to another embodiment of the invention, a known patient sample is used as a control sample/initial test sample. The known patient sample is characterized as having distinguishable populations, e.g. at least two types of cells, that are either similar or identical to the populations to be diagnosed by that particular instrument. In the example of a diagnostic device that will be performing standardized immune monitoring panels, such as that shown in FIGS. 1-6, the known sample will have a cell content that includes the types of cells (e.g. CD4+ T cells) to be analyzed by instrument 10.

According to this embodiment of the invention, once the known patient sample is run through an instrument 10 undergoing evaluation, the results should indicate whether instrument 10 was able to detect a plurality of populations of cells. If the resolution and sensitivity of the instrument are optimized, distinct populations of cells should be indicated in the results. Software can be used to calculate off light scatter, ECV and/or fluorescence data in the manners described herein.

The following is an example of calculations that can be performed on the resulting instrument data to determine how effectively a separation of populations was found. The logarithmic ("log") value of data resulting from two populations detected by the flow cytometer can be used, rather than the raw data, so as to remove the variation between channel number and the standard deviation from the function.

The difference between the mean channel numbers (e.g. between two populations to be observed) is then divided by the difference between the two standard deviation points of the populations, so as to result in a parameter value between negative infinity and 1. For readability, this number is multiplied by 10 and compared to a scale set forth below. The resulting number is referred to herein as a "Population Accuracy Value".

If the two populations are very distinct, i.e. at least 99% of the populations of cells are separated from each other, a Population Accuracy Value between 3-10 will be returned by the calculation. Such a Population Accuracy Value may be considered to indicate the populations have an "excellent" separation.

If the two populations are not as distinct, e.g. if the Population Accuracy Value returned is between 0-3, the separation may be considered "good." This correlates to at least 95% of the populations being separated from each other.

When the Population Accuracy Value returned is 0, this the point at which the standard deviations of the two populations overlap. At this point, approximately 5% of the populations overlap.

When the Population Accuracy Value returned is between −3 and 0, the separation of populations may be considered to be "moderate," since greater than 5% of the populations overlap.

Finally, when the Population Accuracy Value returned falls below −3, the separation of populations may be considered to be "poor," since separation between populations is less clear and results may not be determinative.

The following table is exemplary of a table that can be used by clinicians after the known patient sample is tested to determine whether the flow cytometer is operating optimally.

| Numeric range for Population Accuracy Value | Meaning |
| --- | --- |
| 3-10 | Excellent separation such that >99% of the populations are separated from each other. |
| 0-3 | Good separation >2SD or aprox 95% of the populations are separated from each other. |
| 0 | Point at which the 2SD's of the populations touch. Aprox 5% of the populations overlap |
| −3 to 0 | Moderate separation as greater than 5% of the populations overlap |
| <−3 | Poor separation getting worse as the number get's lower |

By using such a point system, clinicians and/or flow cytometry manufacturers can set a standard value at which flow cytometer service is suggested. This will help eliminate unnecessary service calls that may be caused when flow cytometers fail a hypothetical beads test. Moreover, the disclosed point system will allow clinicians to determine when a flow cytometer device can perform certain tests, but perhaps is not sufficiently optimized to perform other tests.

The improved optimization test disclosed herein is proposed for instrument and flow cytometer quality assurance. The proposed method analyzes population separation for measuring instrument performance. Such a method may also use population separation for measuring sample and/or run quality using similar software calculations of off scatter, ECV and/or fluorescence.

The disclosed embodiment may also be used to derive a statistic to measure the resolution and sensitivity of an instrument 10 for a particular parameter on a particular test and quantify it in terms of sufficiency for running the test. Such a statistic may then be used to determine whether materials used in the test are adequate. For example, the statistic may be used to define the minimum resolution and sensitivity needs from the cytometer/reagent package, and then analyze whether the cytometer/reagent package is performing adequately to run the test on any patient. The statistic may also be used to determine if data from a previous patient sample should be accepted as accurate. The end result may also be a numeric means of qualifying performance for a test.

While the disclosure is susceptible to various modifications and alternative forms, specific exemplary embodiments thereof have been shown by way of example in the drawings and have herein been described in detail. It should be understood, however, that there is no intent to limit the disclosure to the particular forms disclosed, but on the contrary, the intention is to cover all modifications, equivalents, and alternatives falling within the spirit and scope of the disclosure as defined by the appended claims.

A plurality of advantages arises from the various features of the present disclosure. It will be noted that alternative embodiments of various components of the disclosure may not include all of the features described yet still benefit from at least some of the advantages of such features. Those of ordinary skill in the art may readily devise their own implementations of a diagnostic device and method that incorporate one or more of the features of the present disclosure and fall within the spirit and scope of the disclosure.

What is claimed is:

1. A system for analyzing a cellular sample in a specimen tube, the system comprising:
   a well;
   a mixing station including a rocker having an axis of rotation;
   a probe displaceable above the rocker and above the well, the probe having a longitudinal axis;
   a flow cytometer coupled to the well; and
   a processor to control the mixing station, the probe, and the flow cytometer,
   wherein the processor is programmed to direct:
   the rocker to displace the specimen tube in a rocking motion about the axis of rotation, the axis of rotation being perpendicular to the longitudinal axis of the probe;
   the rocker to orient the specimen tube upright;
   the probe to transfer the cellular sample from the upright specimen tube to the well; and
   the flow cytometer to aspirate from the well and to analyze the cellular sample.

2. The system of claim 1 wherein the specimen tube is held in a tube cassette configured to hold a plurality of tubes, wherein the mixing station further includes a cassette holder configured to support the tube cassette, and wherein the rocker is coupled to the cassette holder and configured to displace the specimen tube by displacing the cassette holder.

3. The system of claim 2 further comprising an autoloader coupled to the mixing station, the autoloader including a cassette queue to hold the tube cassette, wherein the autoloader is configured to deliver the tube cassette to the cassette holder of the mixing station.

4. The system of claim 1 wherein the specimen tube includes a cap and the processor is further programmed to direct the probe to pierce the cap to transfer the cellular sample.

5. The system of claim 1 wherein the processor is further programmed to direct the probe to add a reagent to the well.

6. The system of claim 5 further comprising a reagent station configured to support a reagent vial containing the reagent, the probe displaceable above the reagent station,
   wherein the processor is further programmed to direct the probe to transfer the reagent from the reagent vial and, wherein the processor is further programmed to schedule an incubation time for the reagent and cellular sample mixed in the well before directing the flow cytometer to aspirate from the well.

7. The system of claim 1 further comprising a single-axis track coupled to the probe, the single-axis track extending between the well and the mixing station.

8. The system of claim 7 further comprising an interface mechanism coupled to the well, wherein the single-axis track includes a deposit position above the interface mechanism, wherein the well is one of a plurality of wells, wherein the interface mechanism includes a plate base and a rotation axis, the plate base supporting the plurality of wells and the rotation axis disposed normal to the plate base, wherein the processor directs the interface mechanism to position the base with respect to the rotation axis and to rotate the plate base about the rotation axis such that each of the plurality of wells may be aligned beneath the deposit position.

9. The system of claim 1 wherein the sample is a blood sample and the reagent includes an antibody.

\* \* \* \* \*